(12) United States Patent
Abiru et al.

(10) Patent No.: US 6,626,673 B2
(45) Date of Patent: Sep. 30, 2003

(54) ROOT CANAL FILLING MATERIAL REMOVER

(75) Inventors: Masao Abiru, Tokyo (JP); Kimihiko Sato, Tokyo (JP); Takaharu Takeshita, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/998,211

(22) Filed: Dec. 3, 2001

(65) Prior Publication Data

US 2002/0110787 A1 Aug. 15, 2002

(30) Foreign Application Priority Data

Dec. 20, 2000 (JP) ........................................ 2000-387637

(51) Int. Cl.$^7$ ................................................. A61C 5/02
(52) U.S. Cl. ..................................... 433/224; 433/228.1
(58) Field of Search ................................. 433/224, 226, 433/228.1

(56) References Cited

U.S. PATENT DOCUMENTS 3,933,674 A   1/1976  Farnsworth ................. 255/171
5,811,079 A * 9/1998  Yu et al. ........................ 424/52
5,849,680 A * 12/1998 Wong ........................... 510/175

OTHER PUBLICATIONS

WPI Abstract, AN 1989–064952, JP 1–016707, Jan. 20, 1989.
WPI Abstract, AN 1985–267425, JP 60–181003, Sep. 14, 1985.

* cited by examiner

*Primary Examiner*—Kevin Shaver
*Assistant Examiner*—Melba Bumgarner
(74) *Attorney, Agent, or Firm*—Oblon, Spivak, McClelland, Maier & Neustadt, P.C.

(57) ABSTRACT

To provide a root canal filling material remover that can remove a root canal filling material such as a gutta-percha point which is liable to remain in a root apex portion, or a sealer for root canal filling which is liable to enter into a dental pulp of a root canal wall and remain therein, after being removed during the re-treatment of a root canal, in a simple operation, without need of an excessive root canal enlargement operation as has been seen before, the root canal filling material remover contains at least one member selected from limonene, eucalyptus oil, chloroform and xylene, and a surfactant. Further, a polishing material may be added to the root canal filling remover.

16 Claims, No Drawings

ROOT CANAL FILLING MATERIAL REMOVER

BACKGROUND OF THE INVENTION

1. Field of the Invention

The present invention relates to a root canal filling material remover, which is used during removal of a root canal filling material from a root canal when the re-treatment of the root canal is carried out in the dental remedy.

2. Description of the Conventional Art

In the dental remedy, when the treatment for pulp disease or apical periodontitis is carried out, a materially stable substance is filled within a root canal after extirpation of a pulp to seal a space within the root canal and shield an infectious route between the root canal and a periodontal tissue, or between the root canal and an oral cavity, thereby the root canal remedy being done. In carrying out this treatment, a method that is most often employed at present is a method in which a thin needle-like root canal filling material containing a natural gutta-percha and zinc oxide as major components, that is called a gutta-percha point, is filled within a root canal after extirpation of a pulp, and a root canal aperture is then sealed with a cement or the like. This filling method of the root canal using a gutta-percha point is generally effected by a method in which a plurality of gutta-percha points are successively filled within the root canal, that is called a lateral condensation method. At this time, though it is necessary to fill minutely the gutta-percha points within the root canal, the gutta-percha points do not have thorough adhesion to a root canal wall. Accordingly, there is employed a method in which a material that is called a sealer composition for root canal filling is applied to the gutta-percha points and then filled within the root canal to invest a space between the root canal wall and the gutta-percha point, thereby enhancing sealability. One that is widely used as the sealer composition for root canal filling at present is a material containing zinc oxide and eugenol as major components. In addition to the zinc oxide eugenol-based sealer compositions for root canal filling, employed are also natural resin-made sealer compositions for root canal filling containing a low-viscosity polyisoprene or a natural gutta-percha as a major component because they have high adhesion to the gutta-percha points.

Such root canal remedy is aimed at prevention and remedy of disease in the apical periodontal tissue, in which after extirpation of a pulp and infectious root canal treatment, the gutta-percha points are minutely filled and plugged within the root canal to shield a space between the root canal and the apical periodontal tissue from an oral cavity, thereby keeping the root canal in a sterilized state. However, in general, the root canal takes a complicated shape, and three or four root canals may be present per tooth depending on the kind of the tooth. Further, the shape includes various variations such as a flat shape, a barrel shape, and a curved shape, depending on the individual teeth. Accordingly, even when the remedy is carried out using a root canal filling material made of a gutta-percha point and a sealer for root canal filling as described above, it is difficult to prevent invasion of bacteria, resulting in possible occurrence of a toothache or a swelling of gingiva by infection. In such case, it becomes necessary to carry out again the root canal remedy. Then, it is necessary to carry out the root canal treatment such that the root canal filling material filled within the root canal, which is made of a gutta-percha point and a sealer for root canal filling, is removed carefully by a reamer and a file; if required, organic substances within the root canal, such as necrotized and putrefied substances, are cleaned up with a root canal cleaner such as sodium hypochlorite; and the gutta-percha point is again filled by means of the above-described lateral condensation method or other methods.

However, it is very difficult to remove a root canal filling material made of a gutta-percha point and a sealer for root canal filling, which has been filled even in the details of a complicated root canal, by using a reamer and a file. In particular, in the root canal in a flat shape or a curved shape, when the gutta-percha point remains in a root apex portion thereof, the infected portion cannot be thoroughly cleaned so that there is a high possibility that the infection is again spread, resulting in occurrence of a toothache or a swelling of gingiva. In such case, it is necessary to carry out a root canal enlargement operation using a reamer or a file, thereby removing the remaining root canal filling material. Further, the sealer composition for root canal filling is high in fluidity and has adhesion to the root canal, as compared with the gutta-percha point. Accordingly, when the sealer composition for root canal filling enters into a dentinal tubule, it is impossible to remove the sealer composition for root canal filling without enlargement of the root canal, and thus, it is necessary to scrape the sealer composition for root canal filling together with the root canal wall. However, in general, a phenomenon where the root canal filling material remains in the root apex portion is often found in the case where the root canal is in a complicated shape, and hence, it is difficult to visually confirm this phenomenon directly, so that it is very difficult to carry out the root canal enlargement operation. Further, since the amount of the root canal filling material remained in the root canal wall is very little, the root canal filling material is hardly subjected to contrast through X-rays, and an operator hardly understands the state of the root canal enlargement. Thus, the root canal enlargement is a technically difficult operation. In addition, the root canal enlargement involves evils such as lowering in the strength of the root canal, leading to an increase of a danger that the root canal is broken. Accordingly, it has been demanded that the root canal filling material remained within the root canal is removed without carrying out the root canal enlargement as far as possible.

SUMMARY OF THE INVENTION

Under such circumstances, the invention is aimed to provide a root canal filling material remover, by which, after removing a root canal filling material from a root canal using a reamer or a file during the re-treatment of the root canal, the root canal filling material such as a gutta-percha point remained in a root apex portion or a sealer for root canal filling entered into and remained in a dentinal tubule of a root canal wall can be removed through a simple operation without carrying out an excessive root canal enlargement operation as in the conventional art.

In order to achieve the above-described aim, we, the present inventors made extensive and intensive investigations. As a result, it has been found that when a root canal filling material remover comprising a solution capable of dissolving or swelling and softening a resin component, such as a polyisoprene, as a major component of a gutta-percha point or a natural resin-made sealer for root canal filling material to be used in the root canal filling material and of dissolving eugenol zinc as a matrix forming a cured material of a zinc oxide eugenol-based sealer for root canal filling, having a surfactant compounded therein, is applied to a root canal from which the root canal filling material has been removed using a reamer or a file, the root canal filling material remained in the details of the root canal can be removed through dissolution or swelling and softening, without removal by root canal enlargement, and that preferred results are obtained by further adding a polishing material to the root canal filling material remover, leading to accomplishment of the invention.

DESCRIPTION OF THE PREFERRED EMBODIMENTS

Specifically, the root canal filling material remover according to the present invention is a root canal filling material remover comprising at least one member selected from limonene, eucalyptus oil, chloroform and xylene, and a surfactant. Of these, limonene is preferred because it is superior to chloroform and xylene in terms of safety to living bodies and is inexpensive as compared with eucalyptus oil. It is preferred that the amount of the at least one member selected from limonene, eucalyptus oil, chloroform and xylene is in the range of 80 to 99% by weight, whereas the amount of the surfactant is in the range of 1 to 20% by weight. When a polishing material is further added in an amount of 2 to 10 parts by weight to 100 parts by weight of the total sum of the at least one member selected from limonene, eucalyptus oil, chloroform and xylene and the surfactant, in addition to the solubility, the removing properties are improved, and hence, such is preferred.

The limonene that is used for the root canal filling material remover according to the present invention is one of monocyclic monoterpenes, and both of d-limonene and l-limonene can be used. The limonene has a function to swell and soften natural gutta-percha or a polyisoprene as a major component for the gutta-percha point or natural resin-made sealer for root canal filling. Also, since the limonene dissolves styrene therein, the limonene is particularly effective for a root canal filling material having a polyisoprene-styrene copolymer compounded therein.

The eucalyptus oil that is used for the root canal filling material remover according to the present invention is a substance containing, as a major component, cineole obtained by steam distillation of leaves of the genus Eucalyptus plant. The eucalyptus oil has a function to swell and soften the natural gutta-percha or polyisoprene like the limonene.

The chloroform and xylene, each of which is used for the root canal filling material remover according to the present invention, are a substance generally used as a solvent. As the xylene, any of o-xylene, m-xylene and p-xylene can be used. Since the chloroform and xylene have a function to dissolve therein a resin component of natural gutta-percha or a polyisoprene, the removal function thereof is higher than that of the limonene or eucalyptus oil.

Any of the limonene, eucalyptus oil, chloroform and xylene, to be used for the root canal filling material remover according to the present invention, has a function to dissolve therein eugenol zinc as a matrix portion of a cured material of a zinc oxide eugenol-based sealer for root canal filling. Accordingly, even when the root canal remedy is again carried out to a disease when the zinc oxide eugenol-based sealer for root canal filling has been once used, these materials can remove the sealer similar to the gutta-percha point.

It is preferred that the at least one member selected from limonene, eucalyptus oil, chloroform and xylene is compounded in an amount ranging from 80 to 99% by weight in the root canal filling material remover. When the compounding amount is less than 80% by weight, the function to dissolve or swell and soften the root canal filling material tends to be lowered. On the other hand, when it exceeds 99% by weight, the effect of the surfactant is substantially lowered, whereby it tends to become difficult to take out a substance resulted from dissolution or swelling and softening of the root canal filling material, from the inside of the root canal.

The surfactant that is used for the root canal filling material remover according to the present invention is compounded for the purposes of not only having the root canal filling material remover penetrate into the details of the root canal but also effectively removing the dissolved or swollen and softened root canal filling material from the details of the root canal. Particularly, with respect to the limonene or eucalyptus oil, in the case where it is not used together with the surfactant, a substance containing, as a major component, the resin resulted from dissolution or swelling and softening of the root canal filling material attaches to a tooth surface, and it is difficult to take out the substance from the inside of the root canal. Accordingly, it is necessary to use the surfactant.

As the surfactant that is used for the root canal filling material remover according to the present invention, any of anionic surfactants, cationic surfactants, ampholytic surfactants and non-ionic surfactants can be used. Examples of the anionic surfactants include fatty acid soaps, N-acyl amino acids and salts thereof, polyoxyethylene alkyl ether carboxylates, acylated peptides, alkylbenzenesulfonates, sulfosuccinic acid alkyl disalts, polyoxyethylene alkylsulfosuccinic acid disalts, alkylsulfoacetates, N-acyl methyltaurine salts, polyoxyethylene alkyl ether sulfates, secondary higher alcohol ethoxysulfates, and monoglysulfates. Examples of the cationic surfactants include benzalconium salts and imidazolium salts; and examples of the ampholytic surfactants include lecithin and alkylamine oxides. Examples of the non-ionic surfactants include polyoxyethylene glycerin fatty acid esters, polyoxyethylene secondary alcohol ethers, polyoxyethylene polyoxypropylene alkyl ethers, polyoxyethylene castor oils and hydrogenated castor oils, polyoxyethylene fatty acid alkanolamide sulfates, ethylene glycol fatty acid esters, fatty acid monogylcerides, propylene glycol fatty acid esters, sorbitan fatty acid esters, and sucrose fatty acid esters. Of these, preferred are fatty acid soaps, acylated peptides, polyoxyethylene alkylsulfosuccinic acid disalts, secondary higher alcohol ethoxysulfates, monoglysulfates, polyoxyethylene glycerin fatty acid esters, polyoxyethylene castor oils and hydrogenated castor oils, polyoxyethylene fatty acid alkanolamide sulfates, fatty acid monogylcerides, sorbitan fatty acid esters, propylene glycol fatty acid esters, and sucrose fatty acid esters from the standpoint of safety in the case of use in the oral cavity. It is preferred that the surfactant is compounded in an amount of 1 to 20% by weight in the root canal filling material remover. When the amount the surfactant is less than 1% by weight, the penetration properties into the details of the root canal tend to be insufficient, and it tends to be difficult to remove the substance resulted from dissolution or swelling and softening of the root canal filling material from the root canal. On the other hand, even when the surfactant is compounded in an amount exceeding 20% by weight, the effect is liable to be hardly attained.

The root canal filling material remover according to the present invention can be further compounded with a polishing material, thereby adding a physical polishing function in addition to the removal function by the solution. As the polishing material, useful are polishing materials that are generally used in dental polishing. Examples include dibasic calcium phosphate dihydrate and an anhydride thereof, monobasic calcium phosphate, tribasic calcium phosphate, calcium carbonate, calcium pyrophosphate, calcium sulfate, alumina, hydrated alumina, silica-based polishing materials (e.g., precipitated silica, anhydrous alkali metal silicate complexes), aluminum silicate, insoluble sodium metaphosphate, insoluble potassium metaphosphate, tribasic magnesium phosphate, magnesium carbonate, bentonite, zirconium silicate, and synthetic resins (e.g., polymethyl methacrylate). It is preferred that the polishing material is added in an amount of 2 to 10 parts by weight to 100 parts by weight of the total sum of the at least one member selected from limonene, eucalyptus oil, chloroform and xylene, and the surfactant. When the amount of the polishing material is less than 2 parts by weight, the removal effect of the root canal filling material by polishing tends to be hardly attained. On the other hand, when the polishing material is compounded in an amount exceeding 10 parts by weight, there is a possibility that the function to dissolve or swell and soften the root canal filling material by the at least one member selected from limonene, eucalyptus oil, chloroform and xylene is lowered. These polishing materials may be compounded singly or in admixture of two or more thereof.

The root canal filling material remover according to the present invention is used in the following manner. That is, first of all, the gutta-percha point and the sealer for root canal filling, each of which is filled in the root canal, are eliminated by means of a reamer and a file, while paying attention such that the root canal wall is not cut as far as possible. Next, the root canal filling material remover according to the present invention is poured into the root canal, and after standing for a while, the root canal filling material remover within the root canal is washed with water for removal. At this time, particularly in the case where the polishing material is compounded, when the root canal filling material remover is stirred within the root canal using a blade-free instrument such as a lentula and a broach instead of standing, an improvement of the washing effect can be expected. And, after removing the root canal filling material, cleaning is carried out using a root canal cleaner such as a sodium hypochlorite solution, and a root canal filling operation is carried out in the customary manner.

During the removal of the root canal filling material using the root canal filling material remover according to the present invention, there is often found a case that a toothache or a swelling of a gingiva occurs due to invasion of bacteria, etc. Accordingly, when the root canal filling material remover according to the present invention is compounded with a root canal enlargement-assisting component such as urea peroxide, urea, and thioxolon, an effect for eliminating proteins such as cell wastes can be expected. Further, the root canal filling material remover according to the present invention may be used in combination with an organic solvent such as ethanol and isobutyl alcohol, and as a matter of course, colorants and the like may be added so far as the characteristics are not hindered.

Now, the invention will be described in detail with reference to the following Examples, but it should not be construed that the present invention is limited thereto.

EXAMPLE 1 d-Limonene (a trade name: D Limonene N, made by Yasuhara Chemical Co., Ltd.) (97% by weight) was mixed with 3% by weight of a polyoxyethylene glycerin fatty acid ester to prepare a root canal filling material remover. The root canal filling material remover was subjected to the following tests: "Confirmation of solubility or swelling properties" and "Observation within root canal after removal of root canal filling material".

Also, in Examples 2 to 5 and Comparative Example 2, root canal filling material removers with a compounding ratio shown in Table 1 were prepared and then tested in the same manner as in Example 1. The results obtained are summarized and shown in Table 1.

(Confirmation of Solubility or Swelling Properties)

A gutta-percha point (a trade name: GC Gutta Percha Point, made by GC Corporation) having a diameter of 1 mm and a length of 15 mm was immersed in 25 ml of each of the root canal filling material removers of the Examples and Comparative Examples, and after standing at 23° C. for 10 minutes, the state of the gutta-percha point was observed.

A eugenol cement (a trade name: Eugenol Cement, made by GC Corporation) as a zinc oxide eugenol-based sealer composition for root canal filling was mixed and filled in a transparent plastic sheet (10 mm×10 mm×2 mm) provided with a recess having a diameter of 8 mm and a depth of 1 mm, to prepare a sample filled with the eugenol cement within the recess. The sample was immersed in distilled water for 24 hours in a thermostat at 37° C. and then immersed in 25 ml of each of the root canal filling material removers of the Examples and Comparative Examples, followed by stirring at approximately 180 rpm using a stirrer. The state of removal of the eugenol cement from each of the samples one minute and three minutes after stirring was observed.

(Observation Within Root Canal After Removal of Root Canal Filling Material)

A standard human maxillary incisor tooth, which had been preserved in a 10% formalin solution after tooth extraction, was used as a sample. The human maxillary incisor tooth was cut in a tip thereof and subjected to pulp chamber enlargement, followed by subjecting to usual root canal enlargement operation to form a root canal. Into this root canal, filled was a gutta-percha point (a trade name: GC Gutta Percha Point, made by GC Corporation), to which had been applied, as a sealer composition for root canal filling, a eugenol cement (a trade name: Eugenol Cement, made by GC Corporation) comprising a eugenol solution compounded with 0.3% by weight of a dye (Food Blue No. 1, made by Daiwa Kasei Co., Ltd.) for discrimination from a root canal wall, by a lateral condensation method. The resulting sample was immersed in distilled water for 7 days in a thermostat at 37° C. Thereafter, the root canal filling material was carefully removed using a reamer and a file, while paying attention such that the root canal was not enlarged. Then, the root canal filling material remover was poured into the root canal, and the root canal filling material remained within the root canal was removed from the root canal wall using a file, followed by washing with water. The sample was cut, and the inside of the root canal was visually observed. Thus, the state within the root canal after removal of the root canal filling material was evaluated according to the following criteria. Further, an example in which the root canal filling material was removed by means of using a reamer and a file only was designated as Comparative Example 1.

A: It was confirmed that the root canal filling material was removed from the root canal wall.

B: It was confirmed that the root canal filling material remained a little on the root canal wall.

C: It was confirmed that the root canal filling material remained on the root canal wall.

TABLE 1

| | At least one member selected from limonene, eucalyptus oil, chloroform and xylene (% by weight) | Surfactant (% by weight) | Polishing material (part by weight)* | Confirmation of solubility or swelling properties | | Observation within root canal after removal of root canal filling material |
|---|---|---|---|---|---|---|
| | | | | Gutta-percha point | Eugenol-based sealer for root canal filling | |
| Example 1 | d-Limonene: 97 | Polyoxyethylene glycerin fatty acid ester: 3 | — | The gutta-percha point was swollen and collapsed such that it was spread. | Three minutes after the stirring, the sealer was all taken out from the recess. | A |
| Example 2 | d-Limonene: 90 | Polyoxyethylene glycerin fatty acid ester: 10 | — | The gutta-percha point was swollen and collapsed such that it was spread. | Three minutes after the stirring, the sealer was all taken out from the recess. | A |
| Example 3 | Eucalyptus oil: 95 | Sodium dodecylbenzene-sulfonate: 5 | — | The original shape was retained, but upon being contacted, the gutta-percha point was collapsed easily. | Three minutes after the stirring, the sealer was all taken out from the recess. | A |
| Example 4 | Chloroform: 92 | Lecithin: 8 | Calcium carbonate: 8 | The gutta-percha point was dissolved and collapsed in an egg soup-like state. | One minute after the treatment, the sealer was all taken out from the recess. | A |
| Example 5 | d-Limonene: 65 Xylene: 17 | Polyoxyethylene glycerin fatty acid ester: 18 | Alumina: 8 | The gutta-percha point was dissolved and swollen and collapsed in an egg soup-like state. | One minute after the stirring, the sealer was all taken out from the recess. | A |
| Comparative Example 1 | — | — | — | — | — | C |
| Comparative Example 2 | Chloroform: 100 | — | — | The gutta-percha point was dissolved and collapsed such that it was spread. | Even three minutes after the stirring, it was confirmed that the sealer remained slightly in an edge of the bottom. | B |

*Addition amount based on 100 parts by weight of the total sum of the at least one member selected from limonene, eucalyptus oil, chloroform and xylene, and the surfactant.

As is clear from Table 1, in the removal of the root canal filling material using a reamer and a file according to Comparative Example 1, there may be a case where the root canal filling material in the details of the root canal cannot be removed, and hence, there is a high possibility that a swelling of a gingiva and the like again occur. Accordingly, in order to remove the root canal filling material remained in the details, a root canal enlargement operation must be carried out to mechanically remove it. Further, according to Comparative Example 2, it was confirmed that in the case of chloroform that had hitherto been used for the removal of a root canal filling material, the sealer for root canal filling remained within the recess. Also, even after nearly removing the root canal filling material within the root canal, it was not possible to completely remove the root canal filling material by water washing. In contrast, according to Examples 1 to 5, it was confirmed that the gutta-percha point was swollen and softened, and the eugenol cement was dissolved, whereby the root canal filling material could be removed. Further, it was confirmed from the results of the observation within the root canal that the root canal filling material remover according to the present invention can surely remove the root canal filling material.

As described above in detail, the root canal filling material remover according to the present invention is a root canal filling material remover that can remove the root canal filling material remained within the root canal after being removed from the root canal during the re-treatment of the root canal, in a simple operation, without need of an excessive root canal enlargement operation as has been seen before. Accordingly, the root canal filling material according to the present invention is very valuable in contributing to the dental remedy.

While the invention has been described in detail and with reference to specific embodiments thereof, it will be apparent to one skilled in the art that various changes and modifications can be made therein without departing from the spirit and scope thereof.

What is claimed is:

1. A root canal filling material remover composition comprising 100 parts by weight of a root canal filling material remover and 2 to 10 parts by weight of a polishing material, wherein the root canal filling material remover comprises 80 to 99% by weight of at least one compound selected from the group consisting of limonene, eucalyptus oil, chloroform and xylene, and 1 to 20% by weight of a surfactant.

2. The root canal filling material remover composition of claim 1 wherein the root canal filling remover is d-limonene and/or l-limonene.

3. The root canal filling material remover composition of claim 1, wherein the root canal filling remover is eucalyptus oil.

4. The root canal filling material remover composition of claim 1, wherein the root canal filling remover is o-, p-, or m-xylene.

5. The root canal filling material remover composition of claim 1, wherein the surfactant is an anionic surfactant.

6. The root canal filling material remover composition of claim 5, wherein the anionic surfactant is selected from the group consisting of fatty acid soaps, N-acyl amino acids and salts thereof, polyoxyethylene alkyl ether carboxylates, acylated peptides, alkylbenzenesulfonates, sulfosuccinic acid alkyl disalts, polyoxyethylene alkylsulfosuccinic acid disalts, alkylsulfoacetates, N-acyl methyltaurine salts, polyoxyethylene alkyl ether sulfates, secondary higher alcohol ethoxysulfates, and monoglysulfates.

7. The root canal filling material remover composition of claim 1, wherein the surfactant is a cationic surfactant.

8. The root canal filling material remover composition of claim 7, wherein the cationic surfactant is selected from the group consisting of benzalconium salts and imidazolium salts.

9. The root canal filling material remover composition of claim 1, wherein the surfactant is an ampholytic surfactant.

10. The root canal filling material remover composition of claim 9, wherein the ampholytic surfactant is selected from the group consisting of polyoxyethylene glycerin fatty acid esters, polyoxyethylene secondary alcohol ethers, polyoxyethylene polyoxypropylene alkyl ethers, polyoxyethylene castor oils, hydrogenated castor oils, polyoxyethylene fatty acid esters, fatty acid monoglycerides, propylene glycol fatty acid esters, sorbitan fatty acid esters, and sucrose fatty acid esters.

11. The root canal filling material remover composition of claim 1, wherein the surfactant is selected from the group consisting of fatty acid soaps, acylated peptides, polyoxyethylene alkylsulfosuccinic acid disalts, secondary higher alcohol ethoxysulfates monoglysulfates, polyoxyethylene glycerin fatty acid esters, polyoxyethylene castor oils, hydrogenated castor oils, polyoxyethylene fatty acid alkanolamide sulfates, fatty acid monoglycerides, sorbitan fatty acid esters, and sucrose fatty acid esters.

12. The root canal filling material remover composition of claim 1, wherein the polishing material is selected from the group consisting of dibasic calcium phosphate dihydrate and anhydrides thereof, monobasic calcium phosphate, tribasic calcium phosphate, calcium carbonate, calcium pyrophosphate, calcium sulfate, alumina, hydrated alumina, precipitated silica, anhydrous alkali metal silicate complexes, aluminum silicate, insoluble sodium metaphosphate, insoluble potassium metaphosphate, tribasic magnesium phosphate, magnesium carbonate, bentonite, zirconium silicate, and synthetic resins.

13. The root canal filling material remover composition of claim 1, further comprising a root canal enlargement-assisting component.

14. The root canal filling material remover composition of claim 13, wherein the root canal enlargement-assisting component is selected from the group consisting of urea peroxide, urea, and thioxolon.

15. The root canal filling material remover composition of claim 1, further comprising an organic solvent.

16. The root canal filling material remover composition of claim 15, wherein the organic solvent is selected from the group consisting of ethanol and isobutanol.

* * * * *